(12) United States Patent
Kussendrager et al.

(10) Patent No.: US 8,501,236 B2
(45) Date of Patent: Aug. 6, 2013

(54) METHOD FOR PRODUCING A CRYSTALLINE TABLETING ADDITIVE, ADDITIVE THUS OBTAINED AND USE THEREOF

(75) Inventors: Klaas Daniel Kussendrager, Veghl (NL); Henricus Alphonsus Maria Van Den Biggelaar, Veghel (NL)

(73) Assignee: Campina B.V., Zaltbommel (NL)

( * ) Notice: Subject to any disclaimer, the term of this patent is extended or adjusted under 35 U.S.C. 154(b) by 0 days.

(21) Appl. No.: 13/408,359

(22) Filed: Feb. 29, 2012

(65) Prior Publication Data

US 2012/0220764 A1 Aug. 30, 2012

Related U.S. Application Data

(63) Continuation of application No. 10/333,349, filed as application No. PCT/EP01/08394 on Jul. 19, 2001, now abandoned.

(30) Foreign Application Priority Data

Jul. 20, 2000 (NL) ..................................... 1015752

(51) Int. Cl.
*A61K 9/14* (2006.01)
(52) U.S. Cl.
USPC ............................. 424/489; 424/493; 424/496
(58) Field of Classification Search
USPC ................. 424/400, 489, 493, 496; 426/658, 426/680; 514/777
See application file for complete search history.

(56) References Cited

U.S. PATENT DOCUMENTS 3,085,914 A * 4/1963 Santino et al. .................. 127/30
5,382,434 A 1/1995 De Haan et al.
5,534,555 A 7/1996 Meggelaars et al.
5,593,502 A 1/1997 Fuisz et al.
6,589,554 B1 7/2003 Mizumoto et al.

FOREIGN PATENT DOCUMENTS

| EP | 0 124 928 A1 | 11/1984 |
| EP | 0 239 172 A2 | 9/1987 |
| EP | 0 509 606 A1 | 10/1992 |
| JP | 55019237 A * | 2/1980 |
| WO | WO-02/08470 A1 | 1/2002 |

OTHER PUBLICATIONS

Elamin et al., "The use of amorphous model substances to study mechanically activated materials in the solid state," Int'l. J. of Pharmaceutics, vol. 19, 1995, pp. 25-36 [XP-001038043].
International Search Report for PCT/EP01/08394, dated Dec. 28, 2001, 3 pages.
Saleki-Gerhardt et al., "Non-Isothermal and Isothermal Crystallization of Sucrose from the Amorphous State," Pharmaceutical Research, vol. 11, No. 8, 1994, pp. 1166-1173 [XP-001034127].
Sebbatu et al., "Effect of Moisture Sorption on Tabletting Characteristics of Spray Dried (15% Amorphous) Lactose," Pharmaceutical Research, vol. 11, No. 9, 1994, pp. 1233-1238.

* cited by examiner

*Primary Examiner* — Michael G Hartley
*Assistant Examiner* — Micah-Paul Young
(74) *Attorney, Agent, or Firm* — Gilberto M. Villacorta; Sunit Talapatra; Foley & Lardner LLP

(57) ABSTRACT

A method for producing a tableting additive, which method comprises providing a spray dried tableting additive in particulate form which particles at leas partially consist of amorphous additive material and at least partially of crystalline additive material; and crystallising the amorphous additive material by subjecting the particles for a short time and under agitation to a temperature between 30 and 100° C. at a relative humidity between 60 and 25%. More in particular, the relationship between relative humidity and temperature is defined by the formula: % relative humidity=218-47*Ln(T(° C.)), wherein T(° C.) is the temperature to which the particles are subjected.

8 Claims, 7 Drawing Sheets

A.

B

Effect of stabilisation treatment on a given sample of spray dried lactose:
Tableting profiles on Kilian rotary press 15 stations, 30 000 tab/h
250mg tablets 9mm flat punches, Lubrication : 0,5% Mg stearate

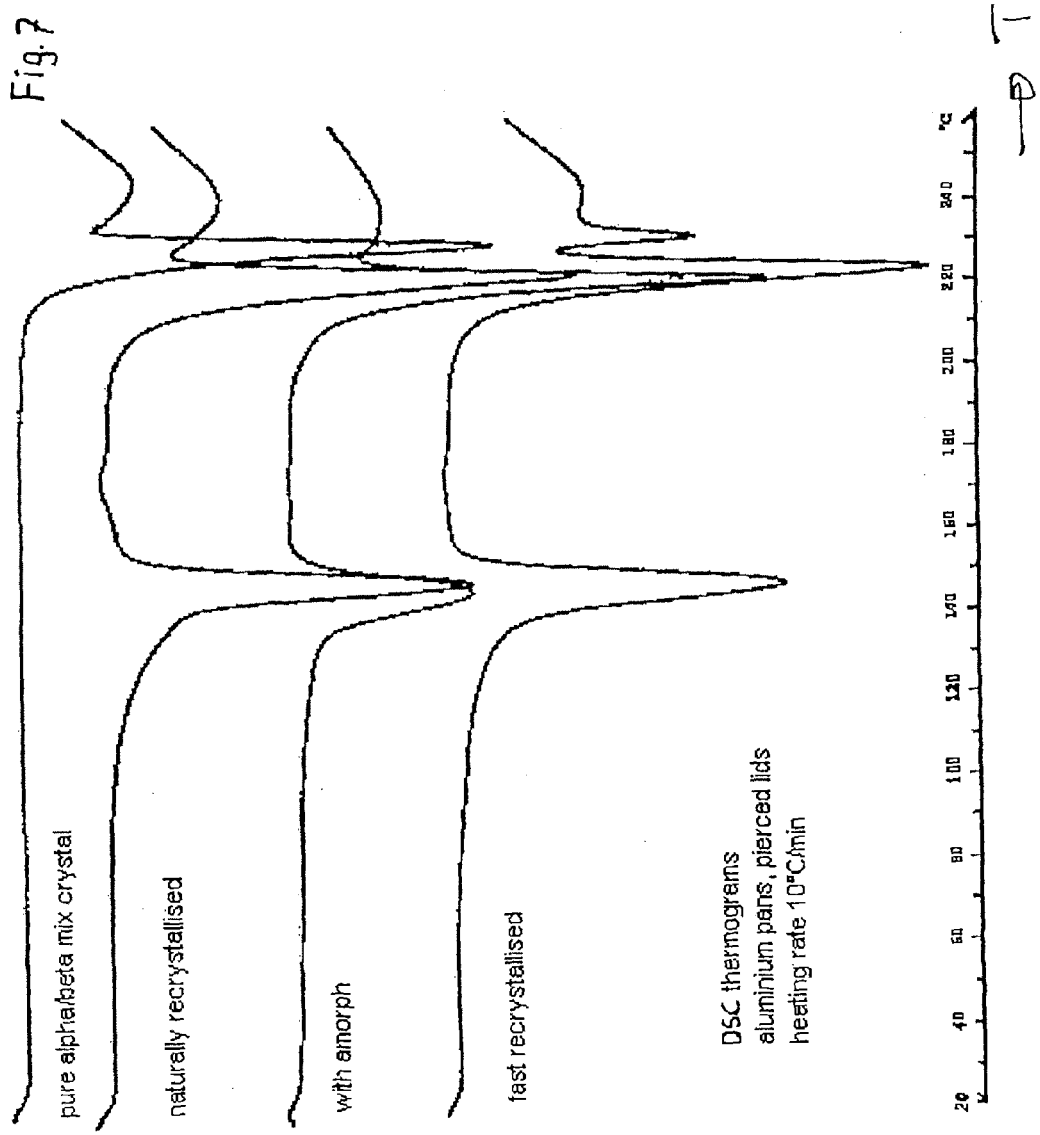

METHOD FOR PRODUCING A CRYSTALLINE TABLETING ADDITIVE, ADDITIVE THUS OBTAINED AND USE THEREOF

CROSS REFERENCE TO RELATED APPLICATIONS

This application is a continuation of U.S. patent application Ser. No. 10/333,349, filed Jul. 21, 2003, which is a National Stage Application of PCT/EP2001/008394/, filed Jul. 19, 2001 and claims priority to Netherlands Patent Application No. 1015752, filed Jul. 20, 2000. The entire contents of each of the aforementioned are incorporated herein by reference.

BACKGROUND OF THE INVENTION

1. Field of the Invention

The invention relates to a method for producing a tableting additive, to the tableting additive thus obtained and to the use of the said additive. The additive is in particular a lactose additive.

2. Description of the Related Art

Usually spray dried materials, such as lactose, consist of crystalline and amorphous material. In the case of lactose, spray dried particles comprise monohydrate lactose and amorphous lactose. Unlike crystalline lactose, amorphous lactose is a hygroscopic material. It will readily take up moisture from the surrounding atmosphere. This moisture uptake reduces the glass transition temperature of amorphous lactose drastically: from 104° C. at 0% moisture content in the amorphous material down to 37° C. with 7.2% moisture content for example and even further down to 5° C. at ca. 14% moisture content. Hence, when the moisture content in the amorphous material has reached a critical value, the glass transition temperature $T_g$ is lower than the ambient temperature, and the amorphous material changes from a glassy state into a rubbery state. Then molecular rearrangements occur and the amorphous material crystallises.

Thus, the amorphous form is not stable and may crystallise into the monohydrate form. When this crystallisation occurs in the presence of the active ingredient, such as a drug, it may become bound in the crystal. For tablets, the disintegration properties are important. When due to the hygroscopic character of the amorphous lactose in the tablets, crystallisation occurs over time, this may affect the disintegration properties and the bioavailability of the active ingredient thus altering the performance of the tablet.

It is therefore desirable to stabilise the tableting additive, such as lactose, in order to avoid changes in bioavailability and disintegration behaviour.

SUMMARY OF THE INVENTION

It was found according to the invention that a method which comprises:

a) providing a spray dried tableting additive in particulate form which particles at least partially consist of amorphous additive material and at least partially of crystalline additive material; and b) crystallising the amorphous additive material by subjecting the particles for a short time and under agitation to a temperature between 30 and 100° C. at a relative humidity between 60 and 25% will lead to a tableting additive that is stable with regard to moisture.

The relative humidity (RH) is to be selected in an indirect proportional manner to the temperature. It was found according to the invention that the relative humidity is preferably as defined by the formula:

$$\% \text{ relative humidity} = 218 - 47 * Ln(T(°C.))$$

wherein $T(°C.)$ is the temperature to which the particles are subjected during the treatment.

More in particular, when the temperature is 36° C., the relative humidity should be more than 50%, when the temperature is 40° C., the relative humidity should lie between 50% and 65%, when the temperature is 47° C., the relative humidity should be about 48%, when the temperature is 53° C., the relative humidity preferably lies between 50% and 65%, when the temperature is 60° C., the relative humidity lies between 31 and 44% and when the temperature is 75° C., the relative humidity should be about 25%.

It was found according to the invention that a fast crystallisation is required to obtain good or even excellent tableting properties. Such fast crystallisation is obtained by treating the additive material for a short time. Preferably, the short time is less than 10 minutes, more preferably, it is less than 5 min, most preferably the short time is about 2 min or less.

During the crystallisation treatment some sort of agitation is required. It was found that good results are obtained when the agitation is provided by a fluid bed device. However, also some sort of mechanical form of agitation, such as stirring can be used.

The method as described herein is found to be particularly suitable when the additive material is lactose. In the examples, the invention will be illustrated with lactose. This does not mean that lactose is the only additive material for which the invention may be used. Other materials are monosaccharides, such as glucose, fructose, mannose etc. and the polyols derived therefrom, like sorbitol, mannitol etc., disaccharides, such as maltose, sucrose and their derivatives, such as maltitol, lactitol (from lactose) and oligo- and polysaccharides, such as dextrins, galacto- oligosaccharides and fructo-oligosaccharides and starches.

The lactose that is used as the starting product in the method of the invention is spray dried lactose. Such spray dried lactose may for example be obtained by means of the method described in EP-239 172, which is incorporated herein by reference. In summary, the method described therein comprises feeding a slurry of crystalline a-lactose hydrate in a saturated lactose solution to a spray drier and drying the same, wherein the selection of the ratio between the amounts of crystalline material and dissolved lactose in the slurry determines the ratio between the amounts of crystalline and amorphous lactose in the spray dried product. The person skilled in the art of spray drying can modify the process conditions to obtain a suitable spray dried product based on his common general knowledge of spray drying. For tableting purposes for pharmaceutical use the lactose is a pharmaceutical grade of lactose, which means that it meets the European, US and Japanese Pharmacopoeial requirements for lactose monohydrate, in particular regarding purity and water content.

The tableting additive obtained according to the method of the invention is substantially free of amorphous material and is preferably completely crystalline, which can be tested by Differential Scanning calorimetry (DSC) in which a thermogram of the lactose shows no crystallisation peak.

About 5-20% of the total lactose additive prepared with the method of the invention constitutes β-lactose. This β-lactose is present in the form of an α/β mix crystal which is demonstrated by the comparison of a DSC thermogram of the additive with a DSC thermogram of pure α/β mix crystal. Both thermograms show the same peak, which corresponds with the melting point (230° C.) of a α/β mix crystal structure (FIG. 7). This peak is not present on the thermogram of conventional spray dried lactose or naturally crystallised lactose.

It was found that at temperatures below 35° C. the content of β-lactose decreases. It may still be that some mix crystal is formed but it is not sufficient for obtaining acceptable tableting properties. The tabletability of the product seems to follow the change in β-lactose content. If this content falls, the tabletability will also decrease. If after crystallisation, the β-lactose content remains constant, the good tableting properties are retained.

Before crystallisation, amorphous lactose is composed of α- and β-lactose. The ratio between α- and β- lactose depends on the ratio that was originally present in the lactose solution that was spray dried. In principle, there is a permanent mutarotation between the two forms in solution, but this equilibrium may be affected by particular parameters, such as temperature, pH etc. Spray drying temperature may thus have an effect on the ratio between α- and β-lactose in the starting product.

The tableting profile is defined as the relationship between tablet crushing strength or tensile strength as a function of compaction force or pressure on a tableting press or a compaction simulator.

In addition to the method, the invention also relates to the additive obtainable by the method. This additive comprises substantially no, preferably no amorphous additive material. The originally present amorphous material is converted at least partially into a mix crystal of α- and β-lactose. The advantages of this additive are that it leads to a tabletability that is equivalent or even better than that of conventional spray dried lactose, but in addition the additive is more stable to moisture than the conventional spray dried lactose.

The invention furthermore relates to the use of the additive for the preparation of tablets.

The present invention will be further illustrated in the examples that follow.

FIG. 7 is a DSC thermogram of various samples.

DESCRIPTION OF THE PREFERRED EMBODIMENTS

EXAMPLES

Example 1

Crystallisation Conditions

Figure 1:
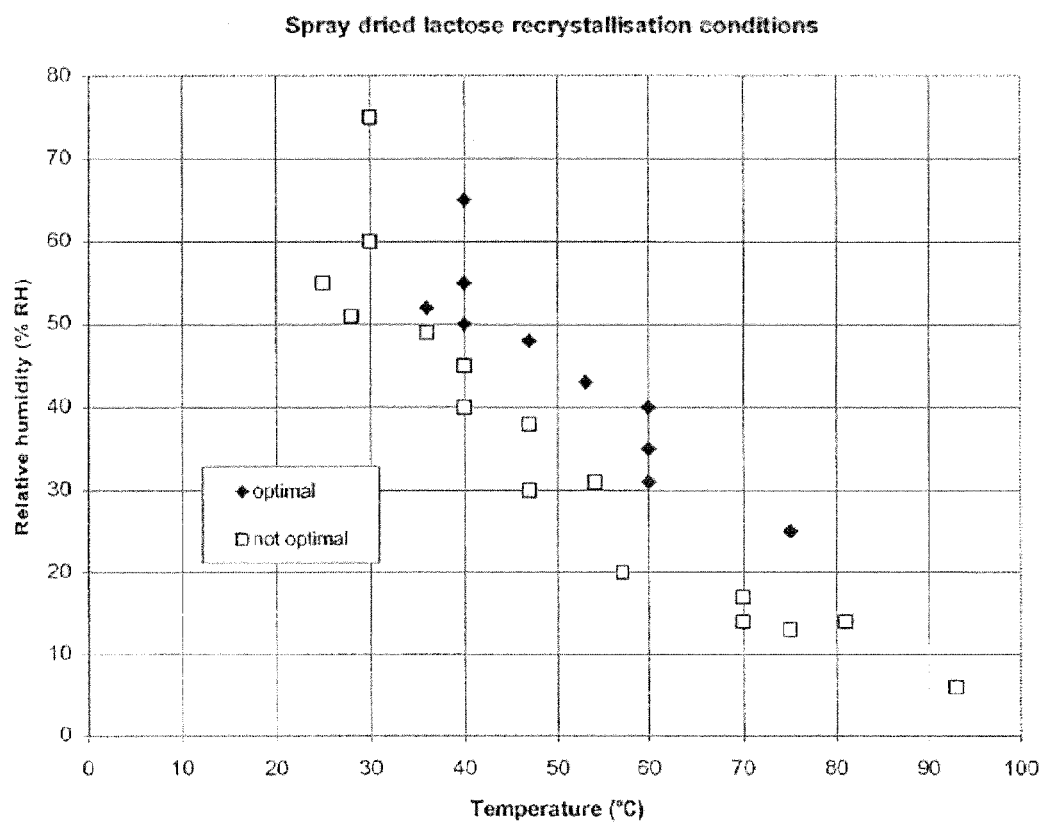
FIG. 1 is a map of crystallisation conditions for stabilising spray dried lactose showing the relationship between temperature and relative humidity.

Stabilisation of the spray dried additive by means of the method of the invention is obtained by conditioning a spray dried lactose sample to various temperatures between 30° C. and 80° C. at various relative humidity conditions. FIG. 1 shows a map of the conditions tested. Filled symbols show optimal conditions and open symbols show non-optimal conditions.

Figure 2:
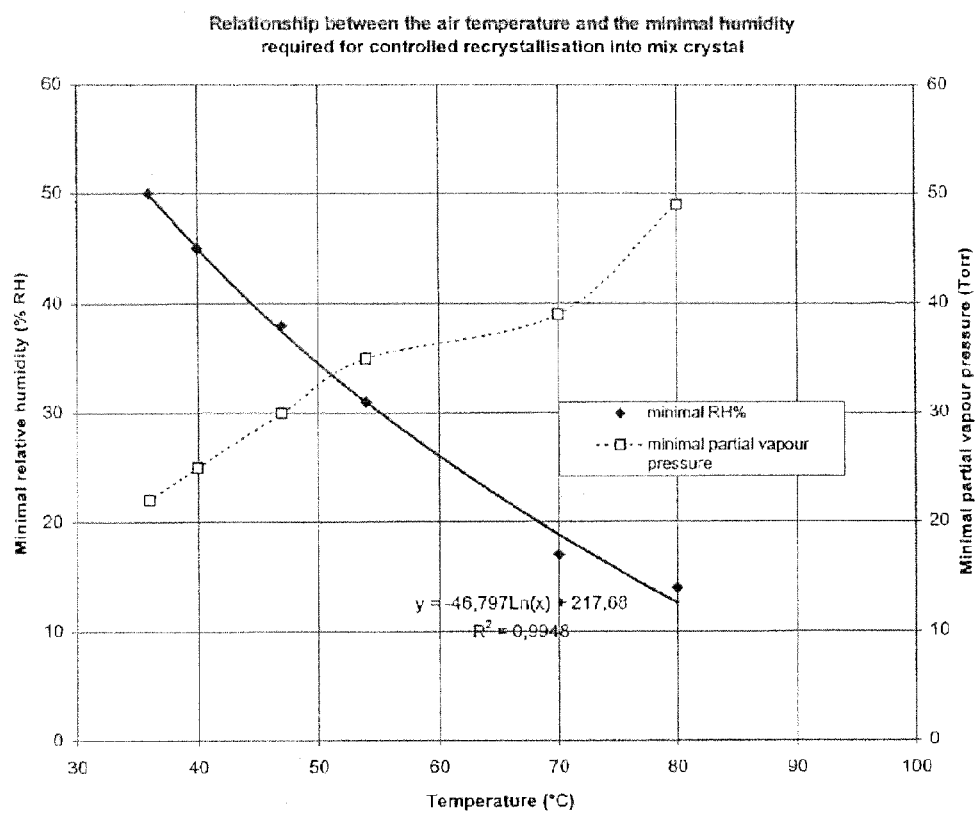
FIG. 2 is a map of the relationship between the air temperature and the minimal humidity required for controlled crystallisation into mix crystal.

FIG. 2 was used to calculate the formula that can be used to determine the relationship between the treatment conditions temperature and relative humidity.

Example 2

Scanning Electron Microscopy

Figure 3:
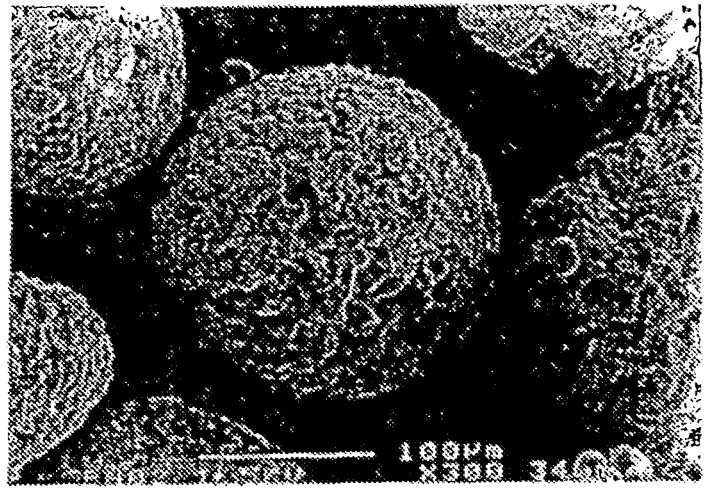
FIG. 3 are Scanning Electron Microscope (SEM) images of conventional spray dried lactose and stabilised spray dried lactose of the invention.
Figure 3:
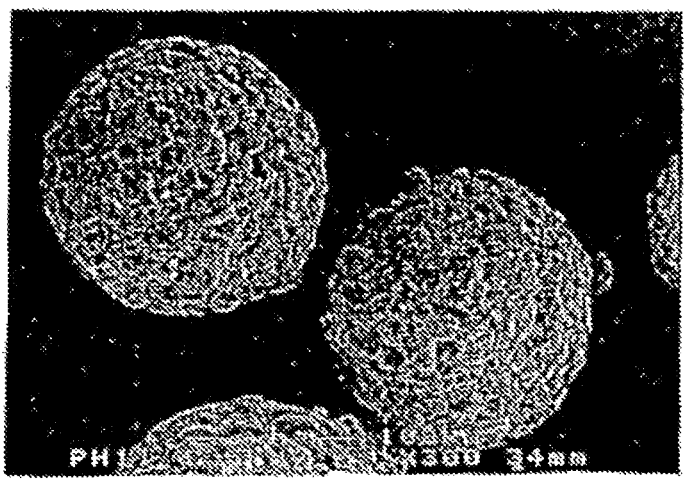

FIG. 3 shows the SEM (scanning electron microscopy) photographs of the various samples. FIGS. 3A and C show different magnifications of conventional spray dried lactose, showing a blurry surface due to the presence of a layer of amorphous lactose embedding the underlying lactose monohydrate crystals. Some tiny spheres (typically <10 μm) amorphous lactose can also be observed on some of the agglomerates. FIGS. 3B and D show different magnifications of stabilised spray dried lactose of the invention, presenting the same agglomerate shape but with a different sub-structure. The amorphous material is no longer present and the picture has gained in sharpness. The crystallised amorphous material has formed a microcrystal structure covering the crystals of lactose monohydrate.

Example 3

Tableting Properties

Various samples of tablets were prepared on a Kilian rotary press 15 stations at 30,000 tablets/hour. The tablets are 250 mg tablets made with 9 mm flat punches and lubrication with 0.5% magnesium stearate.

Figure 4:
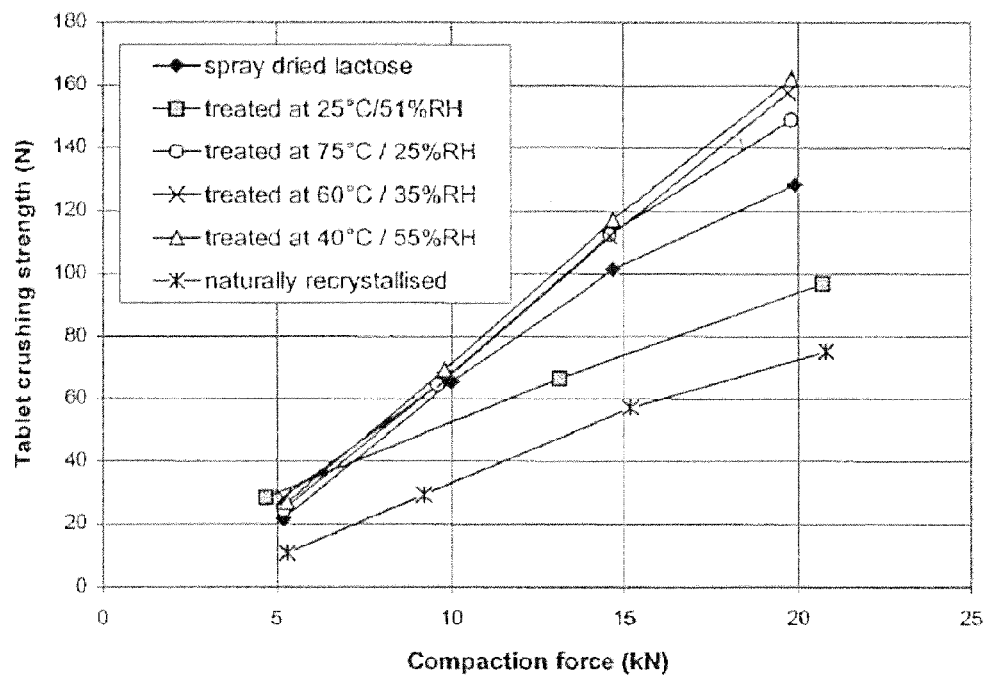
FIG. 4 is a graph showing the effect of the treatment of the invention on a given sample of spray dried lactose.

FIG. 4 presents the tabletability of different samples of spray dried lactose treated under different conditions as follows:

untreated spray dried lactose spray dried lactose left in an open bag to crystallise at ambient conditions (temp. 20-25° C., RH 40-50%, "naturally crystallised")

spray dried lactose crystallised in a fluid bed with various conditions of air temperature and humidity , (25° C./51% RH; 75° C./25% RH; 60° C./35% RH; 40° C./55% RH).

In general the tabletability of the samples treated according to the invention is equivalent to or improved in comparison with the untreated material.

Figure 5:
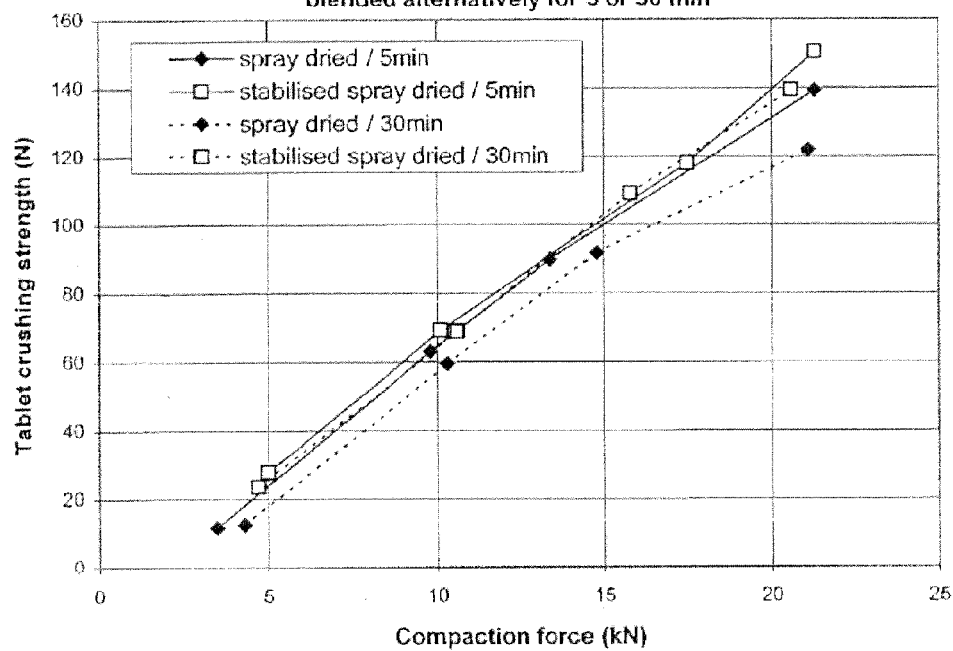
FIG. 5 is a graph showing lubricant sensitivity of a given sample of spray dried lactose.

Spray dried lactose has the disadvantage of being a bit sensitive to the extent of lubrication. Before tableting, powders are always lubricated to facilitate the compression (reduce the friction between die and punches) . The extent of lubrication is determined by the % lubricant used in the mix and the blending time used to lubricate the powders. A longer blending time favors the formation of a continuous film of lubricant on all the external surfaces of the particles. A tableting excipient should be ideally not sensitive to lubrication, meaning that the extent of lubrication would not jeopardise the robustness of the formulation (i.e. a change in lubricant level or mixing intensity would have limited effects on tableting properties) . FIG. 5 shows that the additive of the invention, like lactose monohydrate, is practically insensitive to lubrication extent.

Example 4

Stability

Stabilised spray dried lactose is not hygroscopic. The moisture uptake of this product is almost null over a wide range of relative humidities. This is not true for standard spray dried lactose, due to the presence of amorphous lactose in the product.

Figure 6:
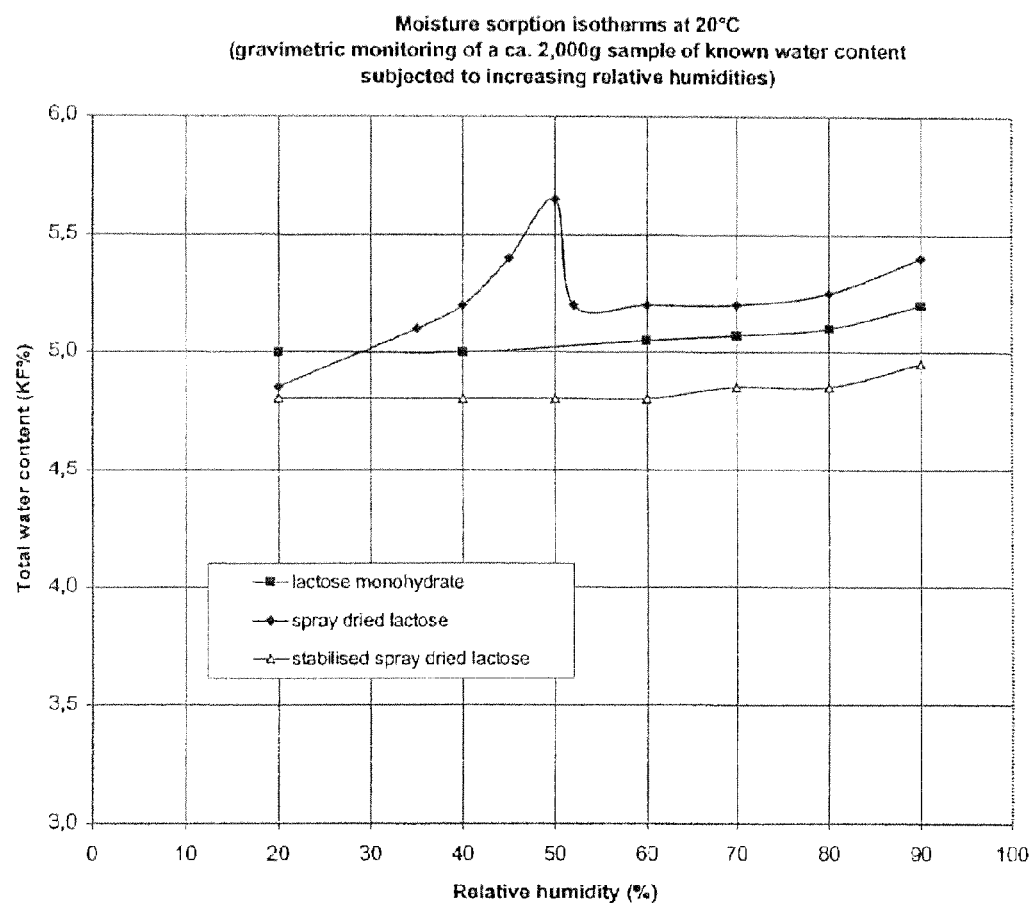
FIG. 6 is a plot of moisture sorption isotherms of various samples of lactose at 20° C.

The moisture sorption isotherms of different lactoses at 20° C. are presented in FIG. 6. The peak at 40-50% RH for spray dried lactose characterises the moisture uptake in the amorphous part, followed by crystallisation and rejection of moisture from the crystal lattice. The additive of the invention, unlike the conventional spray dried lactose, does not take up any additional moisture.

The invention claimed is:

1. A method for producing a crystalline tableting lactose additive, which method comprises:
   (a) providing a spray dried tableting additive in particulate form which particles at least partially consist of amorphous lactose and at least partially of crystalline lactose; and
   (b) converting the amorphous lactose into crystalline lactose by subjecting the particles for a time less than 10 minutes and under continuous agitation by a fluid bed device to a temperature T between 30° C. and 100° C. at a relative humidity between
      (i) a maximum of 60% and
      (ii) a minimum defined by the formula % relative humidity=218−47*Ln(T(° C.), or 25%, whichever is greater,
      wherein 5-20% of the total crystalline lactose obtained is in the form of β-lactose and wherein crystalline tableting lactose additive is substantially free of amorphous material.

2. A tableting lactose additive being in particulate form, wherein the particles comprise substantially no or no additive material in amorphous form, said additive obtained by:
   (a) providing a spray dried tableting additive in particulate form which particles at least partially consist of amorphous lactose and at least partially of crystalline lactose; and
   (b) converting the amorphous lactose into crystalline lactose by subjecting the particles for a time less than 10 minutes and under continuous agitation by a fluid bed device to a temperature T between 30° C. and 100° C. at a relative humidity between
      (i) a maximum of 60% and
      (ii) a minimum defined by the formula % relative humidity=218−47*Ln(T(° C.), or 25%, whichever is greater,
      wherein 5-20% of the total crystalline lactose obtained is in the form of β-lactose and wherein crystalline tableting lactose additive is substantially free of amorphous material.

3. The tableting additive according to claim 2, wherein β-lactose is present substantially in the form of α/βmix crystal.

4. A method of preparing tablets, comprising:
   (a) providing a spray dried tableting additive in particulate form which particles at least partially consist of amorphous lactose and at least partially of crystalline lactose;
   (b) converting the amorphous lactose into crystalline lactose by subjecting the particles for a time less than 10 minutes and under continuous agitation to a temperature T between 30° C. and 100° C. at a relative humidity between
      (i) a maximum of 60% and
      (ii) a minimum defined by the formula % relative humidity=218−47*Ln(T(° C), or 25%, whichever is greater,
      wherein 5-20% of the total crystalline lactose obtained is in the form of β-lactose and wherein crystalline tableting lactose additive is substantially free of amorphous material; and
   (c) preparing the crystalline lactose from (b) into a tablet.

5. The method according to claim 1, wherein all of the amorphous lactose is converted into crystalline lactose.

6. The method according to claim 4, wherein all of the amorphous lactose is converted into crystalline lactose.

7. A tableting additive being in particulate form, wherein the particles comprise substantially no or no additive material in amorphous form, said additive comprising 5-20% β-lactose based on the total lactose content, wherein the β-lactose is present substantially in the form of α/βmix crystal, the remainder being lactose monohydrate particles and a maximum of 5% water.

8. A tablet comprising a tableting lactose additive being in particulate form, wherein the particles comprise substantially no or no additive material in amorphous form, said additive obtained by:
   (a) providing a spray dried tableting additive in particulate form which particles at least partially consist of amorphous lactose and at least partially of crystalline lactose; and
   (b) converting the amorphous lactose into crystalline lactose by subjecting the particles for a time less than 10 minutes and under continuous agitation by a fluid bed device to a temperature T between 30° C. and 100° C. at a relative humidity between
      (i) a maximum of 60% and
      (ii) a minimum relative humidity defined by the formula % relative humidity=218−47*Ln(T(° C.)), or 25%, which ever is greater,
      wherein 5-20% of the total crystalline lactose obtained is in the form of β-lactose and wherein crystalline tableting lactose additive is substantially free of amorphous material.

\* \* \* \* \*